(12) United States Patent
Fischer

(10) Patent No.: US 7,160,271 B2
(45) Date of Patent: Jan. 9, 2007

(54) PROTECTION DEVICE FOR CANNULAE

(75) Inventor: Herwig Fischer, Poznan (PL)

(73) Assignee: Ina Fischer, Monchengladbach (DE)

( * ) Notice: Subject to any disclaimer, the term of this patent is extended or adjusted under 35 U.S.C. 154(b) by 72 days.

(21) Appl. No.: 10/476,912

(22) PCT Filed: May 1, 2002

(86) PCT No.: PCT/DE02/01581

§ 371 (c)(1),
(2), (4) Date: Nov. 3, 2003

(87) PCT Pub. No.: WO02/089877

PCT Pub. Date: Nov. 14, 2002

(65) Prior Publication Data

US 2004/0133170 A1    Jul. 8, 2004

(30) Foreign Application Priority Data

May 5, 2001    (DE) ................................. 101 21 949

(51) Int. Cl.
*A61M 5/32* (2006.01)
(52) U.S. Cl. ....................................................... 604/192
(58) Field of Classification Search .......... 604/164.08, 604/198, 110, 181, 263, 192, 187
See application file for complete search history.

(56) References Cited

U.S. PATENT DOCUMENTS

| 4,795,432 A | * | 1/1989 | Karczmer ................... 604/110 |
| 4,820,277 A |   | 4/1989 | Norelli |
| 4,998,922 A | * | 3/1991 | Kuracina et al. ........... 604/192 |
| 5,324,302 A | * | 6/1994 | Crouse ........................ 606/181 |
| 5,421,347 A | * | 6/1995 | Enstrom ...................... 600/567 |
| 6,409,706 B1 | * | 6/2002 | Loy ............................. 604/198 |

* cited by examiner

*Primary Examiner*—Manuel Mendez
(74) *Attorney, Agent, or Firm*—Andrew Wilford

(57) ABSTRACT

A syringe has a body on which is mounted an end fitting fixed to a needle having a tip. A protective device for the syringe has a small-diameter sleeve fitting around the needle and having an inner end at the end fitting and an opposite outer end. This sleeve can move from a starting position with the outer end adjacent the body and exposing the needle tip and an end position with the outer end engaged over the needle tip. The sleeve is formed with at least one flexible extension having a free outer end generally level with the needle tip in the starting position. The sleeve is secured to the end fitting in the starting position by structure sufficiently weak that a traction applied to the flexible extension displaces the sleeve into the end position.

15 Claims, 8 Drawing Sheets

PROTECTION DEVICE FOR CANNULAE

CROSS REFERENCE TO RELATED APPLICATIONS

This application is the US national phase of PCT application PCT/DE02/01581, filed 1 May 2002, published 14 Nov. 2002 as WO 02/089877, and claiming the priority of German patent application 10121949.0 itself filed 5 May 2001.

FIELD OF THE INVENTION

The invention relates to a protective device for a needle having a tapered end fitting that can be fitted on a complementary tapered mount of a syringe.

BACKGROUND OF THE INVENTION

In order to inject active substances, syringes are used that have a piston-holding cylinder whose front end is provided is with a central or offset tapered mount over which can be slipped the tapered seat of an end fitting of a metallic needle. Such syringes are used in large numbers as so-called single-use syringes that are disposed of after use.

The needle and its end fitting are sealed in a sterile packing and held in a protective cap formed as a quiver-like sleeve having an open end whose internal dimension is such that it can fit tightly over the outer surface of the tapered mount. The doctor and medical staff are thus protected when unpacking the needle and fitting it to the syringe end mount. Once the tapered end fitting is secured to the end mount of the syringe, the protective cap is pulled off so that an injectable substance can be drawn in and then used for a subcutaneous, intravenous, or intramuscular injection or so as to draw body fluids, normally blood, from the patient. In order to prevent needle sticks after use, the cap is fitted back over the front needle end, the end fitting of the needle is pulled off the syringe, and the needle inside the protective cap is thrown out. The protective cap is made of plastic and is formed such that it does not bend even when severely stressed nor can it expose the needle tip. There remains however as a result of the small inside diameter of the protective cap the danger that the sharp needle end misses it to create a substantial danger of injury and a high risk of infection.

Medical personal are normally working very quickly and are occupied with the patient, so that the needle is set aside after use. The used needle is left unprotected on the table and is often tossed as an "open needle" into the trash. When the trash is emptied by the cleaning personnel the needle pokes easily through the plastic garbage bag and can easily injure the personnel dealing with the trash since the needles and syringes are not visible from outside.

In order to prevent this, German 3,904,559 (US equivalents U.S. Pat. Nos. 4,820,277, 4,909,791, and 4,909,972) proposes a protective sleeve for the needle of a syringe that is formed of two pivotal jaws that can be locked to each other so as to enclose the syringe needle in a tube-like space. The jaws are pivoted on the body of the syringe, on a separate adapter, or on the bases of a specially designed syringe needle. The disadvantage of this solution is that it is technically complex and, in particular relative to standard production costs, expensive since the half-shell jaws must be locked together.

It has been proposed for injection needles that the needle be mounted on the piston in its full-forward position so that it can be drawn back into the empty cylinder. A complex coupling is needed that not only increases the cost of the end product but also makes using the needles after use more difficult, requiring at least particular attention and careful handling when fitting the needle end fitting to the piston.

It has further been suggested to provide a longitudinally slidable sleeve on the syringe body that is pulled forward after the syringe is used and closed so that the needle point is covered. The disadvantage of this system is that the diameter of the syringe in increased (by double the wall thickness of the sleeve), the tapered end fitting cannot be mounted at the very end of the syringe body, and it does not rule out the accidental insertion of a finger into the sleeve. Even such an embodiment is not only expensive because of the considerable material used, but in particular because of the closure.

OBJECT OF THE INVENTION

It is therefore an object of the present invention to provide a protective device of the described type that is sufficiently safe, easy to use, and inexpensive to manufacture.

SUMMARY OF THE INVENTION

This object is achieved by the protective device in that the end fitting carries a sleeve that can be pulled into an end position in which the sleeve completely covers the needle tip. By mounting the sleeve on the end fitting it has to start with the smallest possible diameter so as not to present a large opening at its end. It can be made with little material. In addition the sleeve can be provided with pulling means that are no bother and that can be gripped at a safe spacing from the sharp sharpened needle end without any danger of injury.

Thus according to a preferred embodiment of the invention the sleeve is connected with the tapered end fitting by a weakened region. The weakened region is formed as a very thin annular region that connects the tapered mounting part and the sleeve. Alternatively the sleeve is simply fitted frictionally over the end fitting so that once the friction is overcome it can be pulled off. This can be achieved for example by frictionally engaging tapered surfaces. It is significant that the sleeve is no hindrance when injecting or on drawing bodily fluids and a sufficient length of the needle is exposed. Once the friction connection is released or the weakened region is broken, the sleeve can be pulled "forward" in order to safely contain the tip.

Preferably between the sleeve and the end fitting there is a tether, preferably at least one strand or string, whose length is such that it limits movement of the sleeve away from the end fitting beyond an end position. The maximum possible length of the string thus forms a stop by means of which the sleeve is brought into the desired position.

In order to protect the needle tip when it is unpacked and before it is fitted to the tapered mount of a syringe, a sleeve-shaped protective cap is used that is loosely fittable over the needle and that has an open end formed with a lateral slots of a width big enough for the tethers to pass through. When for example there are two diametrally opposite strings fixed on the end fitting, the slits of the protective cap are also diametrally opposite so that the strings fit through them. At its simplest, one tether, that is a string or strand, is enough but two tethers are safer since they allow one string to be torn off.

Since the end fitting with two (or more) slots is less stable with respect to lateral bending, the end fitting has at least two external tongues that are seatable in complementarily formed pockets formed at an open end of the protective cap.

According to an alternative solution the sleeve is elastically or plastically extendable such that a top of the needle that is exposed briefly is completely covered by the sleeve before and after standard use after drawing a bodily fluid or after injecting an active agent. For example the sleeve can be formed over at least a portion of its length as a bellows that provides the desires extensibility. The sleeve can also be formed as a small-diameter extensible telescope. Preferably the sleeve is readily bendable and is made of a material that is strong enough that it cannot be pierced by the needle. If the sleeve is pulled over the needle tip, its bendability leads to a modest deflection to the side so that the pointed needle end in particular its very sharp point, digs into the plastic inner surface of the sleeve and thus effectively prevents a retraction of the part that would expose the tip. In order to effectively protect the pointed needle tip before standard use, a sleeve-shaped protective cap is provided for the needle that can be fitted over the free end of the sleeve and fit with its taper.

Preferably the sleeve has a tentacle-shaped extension that in a starting condition, that is before standard use of the needle, ends level with or slightly, e.g. 1 cm, past the needle tip and that is formed as actuating means for applying traction. This can be a plastic strand or a flat extension that is elastic or flexible but bendable so that it does not interfere with injecting or blood drawing. The tentacle-like extensions form a system that in fact is used automatically. After inserting the needle in a vein, artery, or muscle, before bandaging the puncture site it is standard for the doctor or medical assistant (nurse, aide, etc) to apply a pad to the puncture site as the needle is pulled out. Application of the pad presses down the tentacle-like extensions so that as the needle is pulled out the sleeve is automatically pulled over the needle tip. At this time the tentacle-like extensions have done their job. The strength of the tentacle-like extensions or their tensile strength must not be too great so that the tension serves merely to stretch the sleeve along the needle. The tentacle-shaped extensions are positioned relative to the needle tip, e.g. spaced some 5 mm, such that when the pad is applied to the puncture site these extensions are engaged (right and/or left).

In order to ensure that the needles always lies in the desired plane, the end fitting and the syringe mount are rotation symmetrical.

Preferably the sleeve has an inner wall provided with tongue-shaped spring elements that in an end position covering the needle tip are engageable in pockets on movement of the part and resist opposite movement of the part. Such "barbs" are for example known for use on the outside of anchors for screws. In this case the spring elements do not project radially outward, but radially inward.

According to a further feature of the invention the sleeve has at an end on an inner surface annular niches in which the needle tip fits on return movement of the sleeve so as to prevent further return movement.

BRIEF DESCRIPTION OF THE DRAWING

Embodiments of the invention are shown in the drawing. Therein.

SPECIFIC DESCRIPTION

Figure 1:
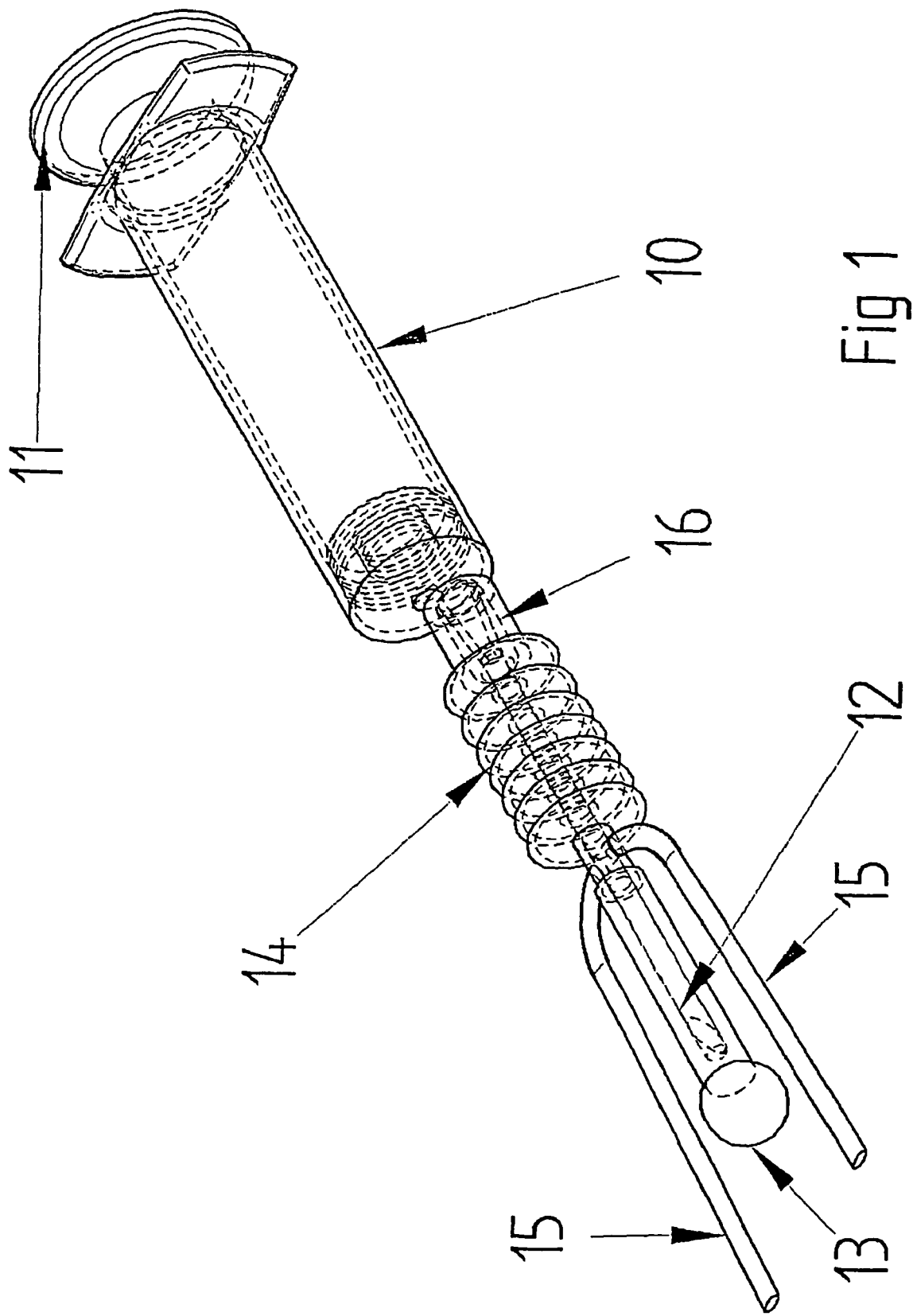
FIGS. 1 and 2 show a first embodiment of the invention respectively before and after standard use of the needle in a partly sectional perspective view.
Figure 2:
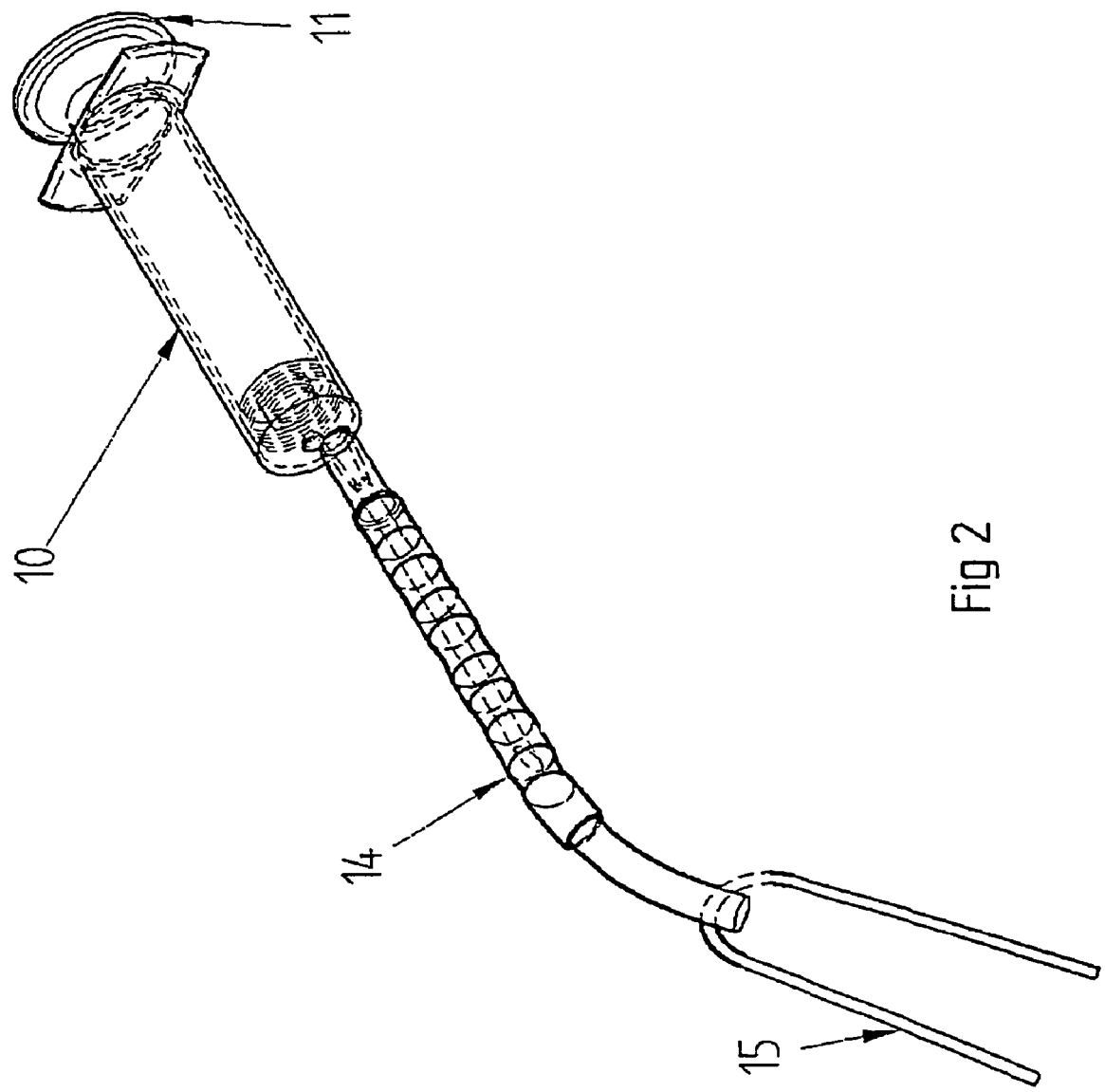
Figure 3:
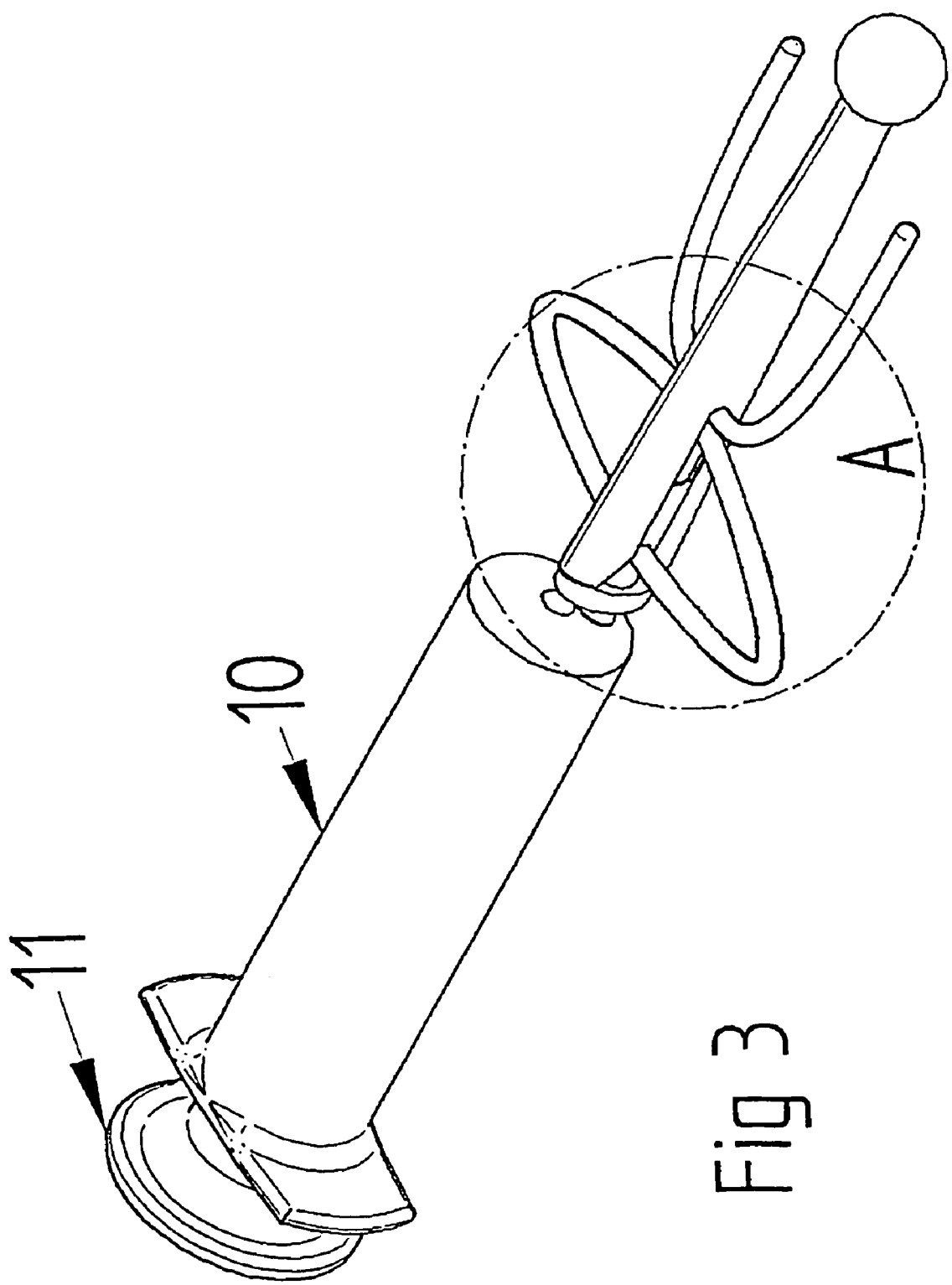
FIG. 3 is a perspective view of another embodiment according to the invention.

The syringe shown in FIGS. 1 and 2 is comprised of a cylinder 10 holding a piston 11 and provided at one end with an eccentric tapered mount over which can be fitted a complementary tapered end fitting 16 in which a needle 12 is imbedded. According to the invention the end fitting 16 carries a sleeve or bellows 14 whose front end is provided with tentacle-like extensions 15 that extend parallel to the needle 12 and even in this case slightly past it. The needle tip and the uncovered parts are covered by a sleeve-like protective cap 13 whose open rear end is fitted over a complementarily shaped cylindrical or tapered surface of the sleeve-like part 14. The needle 12 is thus covered along its full length. As a rule the needle 12 is packed with the end fitting 16, protective cap 13, and bellows 14 separately from the cylinder 10 and piston 11. Once the parts 10 and 11 and the parts 12–16 are separately unpacked the tapered end fitting 16 is fitted to the tapered mount of the syringe cylinder 10 so that the needle 12 is connected to the cylinder 10. Now the protective cap 13 is pulled off so that the needle tip is exposed. After the injectable medicament is drawn in through the needle 12, the medicament is injected subcutaneously, intravenously, or intramuscularly. As this is done the tentacle-like extensions 15 are pushed easily to the side by the skin and offer no hindrance to the injection procedure of the needle even with a complex intravenous procedure. Once the injection is complete, as the needle 12 is withdrawn a swab is applied to prevent bleeding. Application of the swab to the skin holds down the tentacle-shaped extensions 15 so that, as the syringe is backed off, the bellows 14 is expanded to reach the position of FIG. 2 in which it is pulled over the needle tip. The bendable construction of the bellows 14 ensures that, on any movement of the needle 12 forward, the sleeve 14 bends to the side and is not pierced. When bent to the side as shown in FIG. 2 the needle 12 digs into the inside wall of the sleeve 12 that is formed of such a strong material that the needle 12 cannot pierce through it. Even when pushed strongly the needle 12 will at worst bend or break so that all pointed sharp parts are held inside the sleeve 14.

Figure 7:
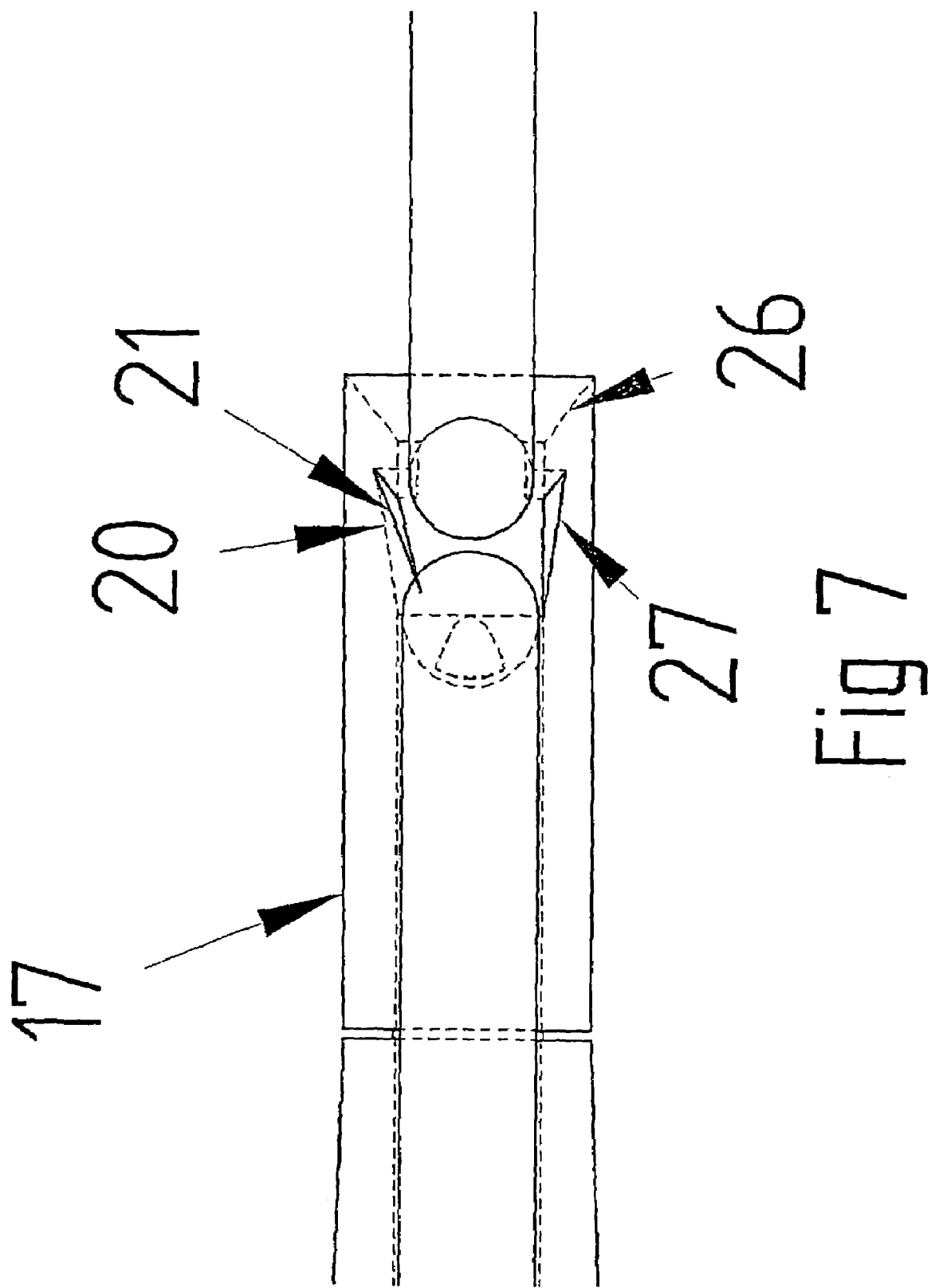
FIG. 7 is a section through a sleeve with barbs.
Figure 8:
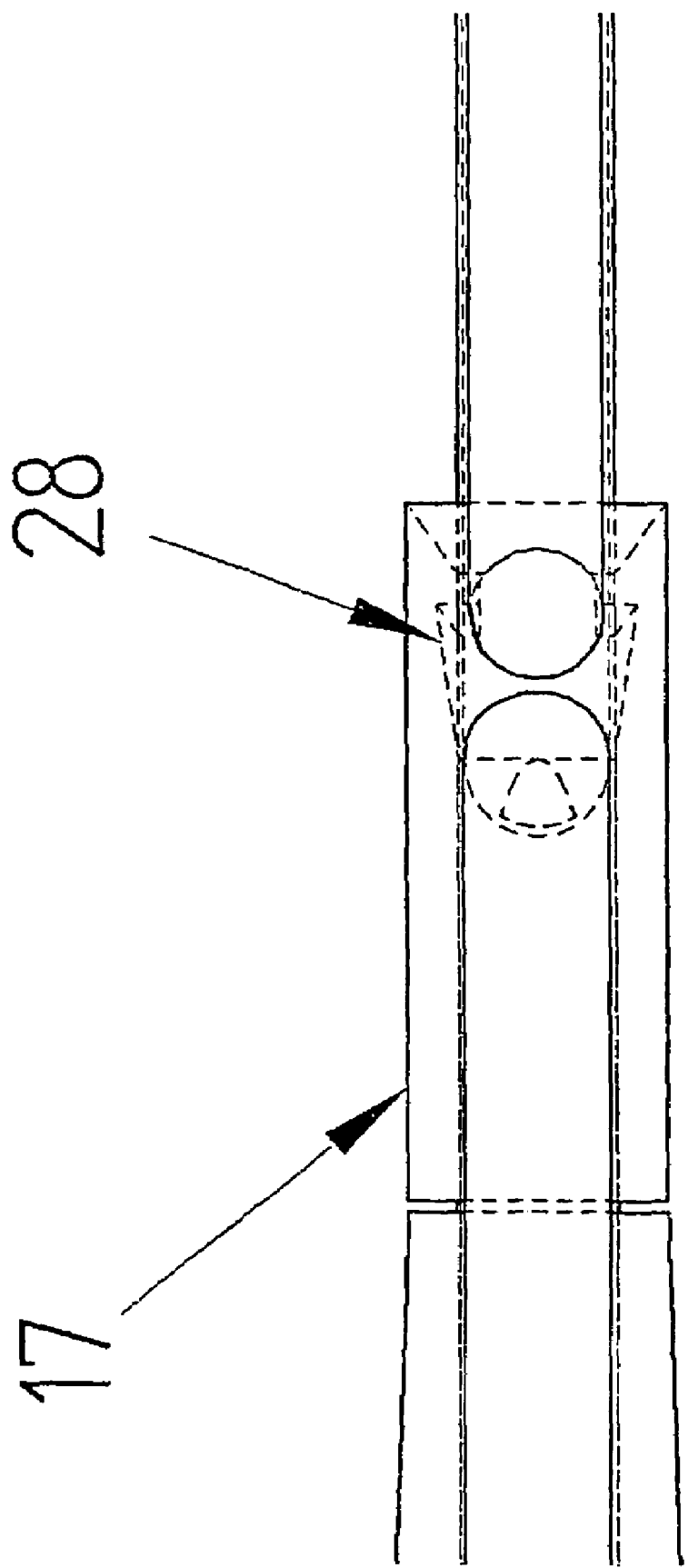
FIG. 8 is a section through a sleeve with an internal annular recess.

In the embodiment of FIGS. 3 to 6 the tapered end fitting 16 is provided with a sleeve part 17 but a joint 18 to it is formed with a very thin wall thickness. A pull on the sleeve 17 ruptures the joint 18 and thus the connection to the tapered end fitting 16 so that the sleeve 17 can slide along the needle 12 until it uncovers the tip of the needle 12. Here also the tentacle-shaped extensions 15 function on or shortly after withdrawal of the needle 12 from the injection site to pull, first to break the weakened joint 18 and subsequently to move the sleeve 17 over the needle tip. Tethers 19 ensure that the part 17 is only moved to the region of the needle tip. The sleeve 17 has internal pockets 20 in which spring elements 21 and 27 can engage when the sleeve 17 is moved toward the tip of the needle 12. FIG. 17 shows the spring element 27 engaged in such a pocket 20 as well as the spring element 21 when spread. In an alternative arrangement shown in FIG. 8 an annular recess or groove 28 in the sleeve inner surface is provided forming a tapered widened region adjacent a restricted-diameter region. When the sleeve-shaped extension 17 is pulled past the needle tip, opposite movement of the needle engages the needle tip in the recess 28. FIG. 7 also shows a tapered widened region 26 that serves for centering the needle in the sleeve.

Figure 4:
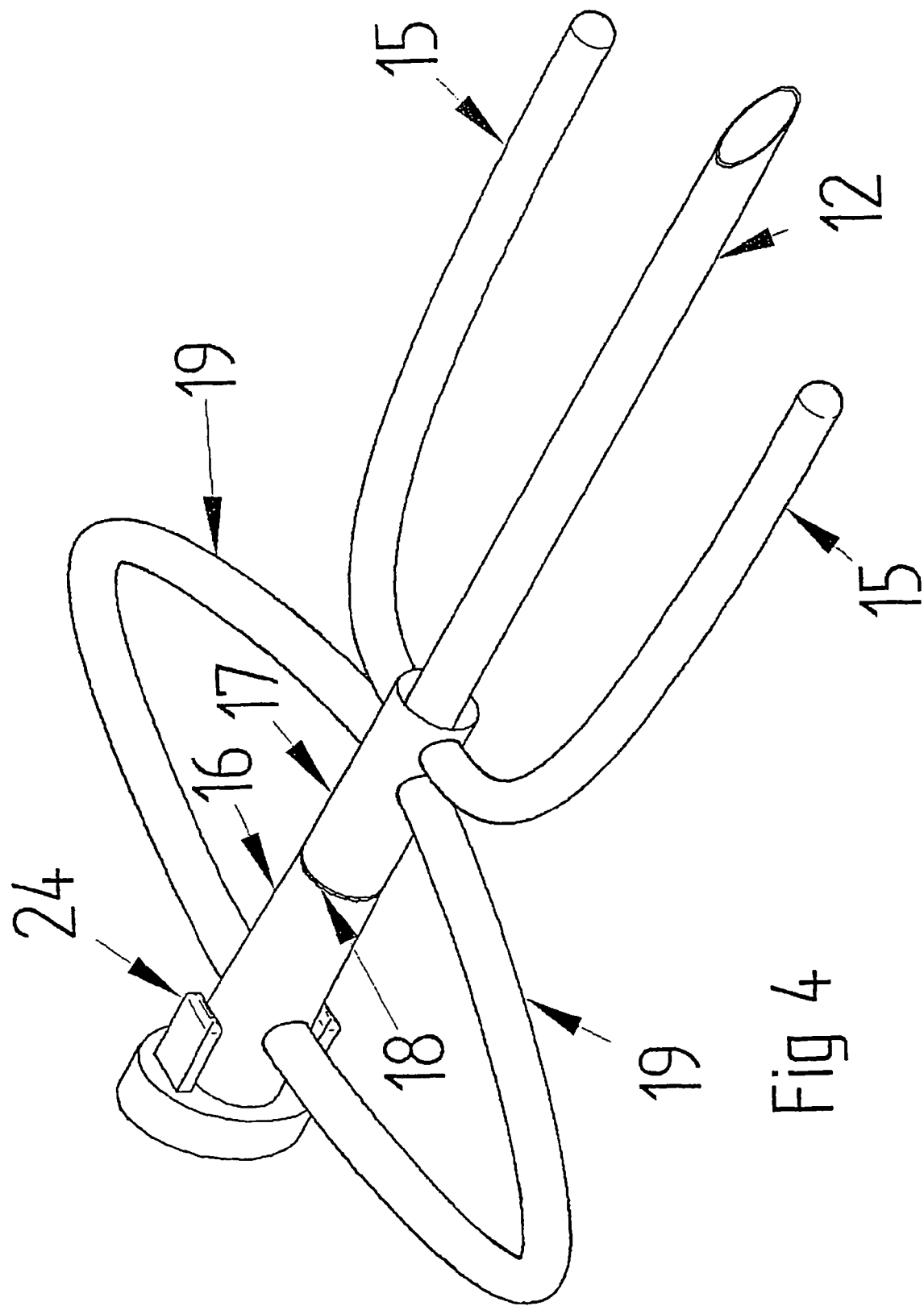
FIG. 4 is a detail view of a tapered end fitting with a sleeve, tethers, and tentacle-like extensions.
Figure 5:
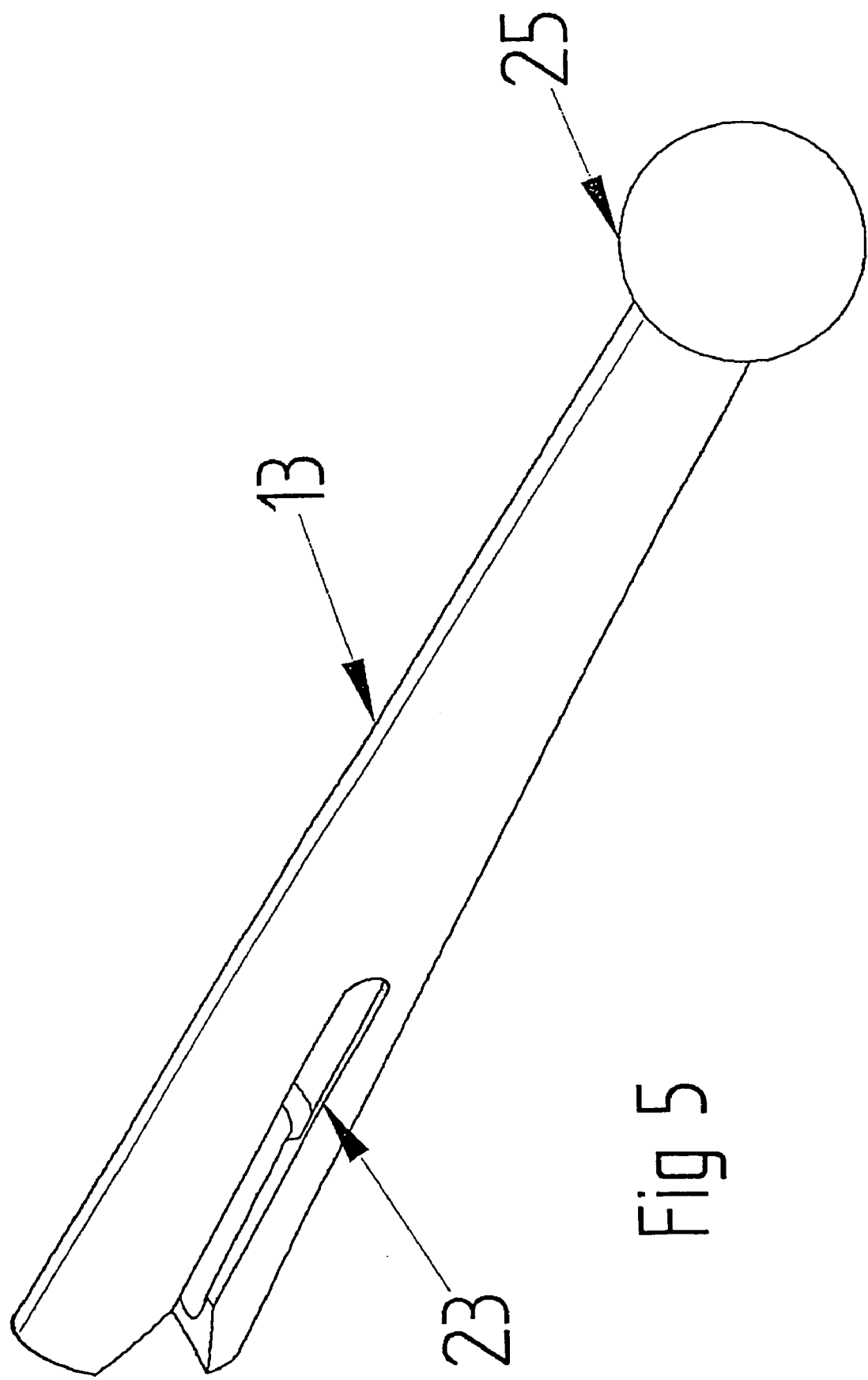
FIG. 5 is a perspective view of a protective cap.
Figure 6:
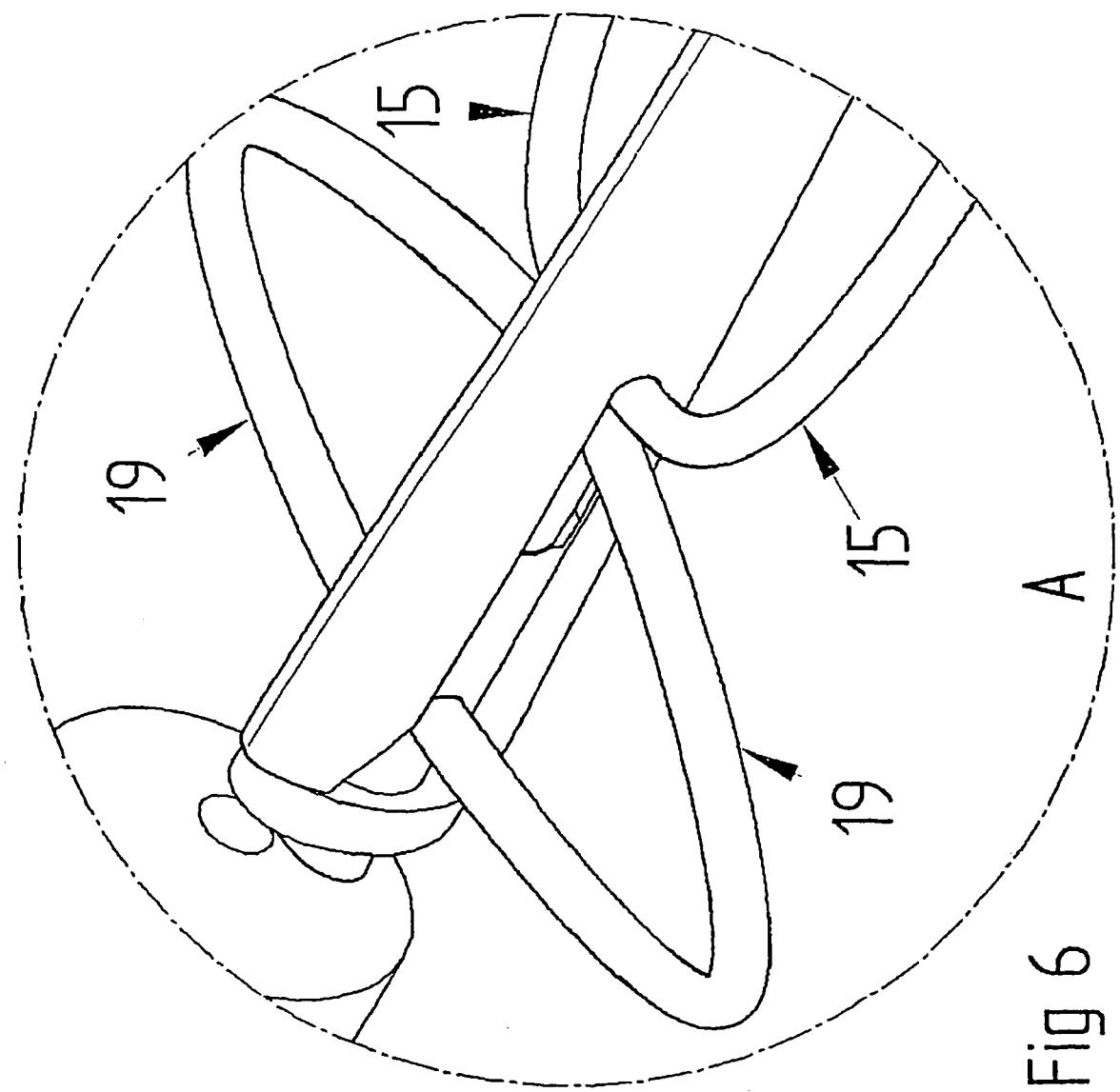
FIG. 6 is a view of detail A of FIG. 3.

FIG. 5 shows a protective cap 13 that has on opposite sides two slots 23 through which the tethers 10 or the ends of the tentacles 15 can fit (see in particular FIG. 6). In addition and as shown in FIG. 4 two tongues 24 are provided on the end fitting 16 that fit in respective unillustrated pockets of the protective cap 13 and prevent this protective cap 13 from bending. The protective cap's closed end has a thickening 25 to surely prevent any piercing by the sharp needle tip.

The invention claimed is:

1. In combination with a syringe having a body on which is mounted an end fitting fixed to a needle having a tip, a protective device comprising:
   a small-diameter sleeve fitting around the needle and having an inner end at the end fitting and an opposite outer end, the sleeve being displaceable from a starting position with the outer end adjacent the body and exposing the needle tip and an end position with the outer end engaged over the needle tip, the sleeve being formed with at least one flexible extension having a free outer end generally level with the needle tip in the starting position; and
   means including structure for securing the sleeve to the end fitting in the starting position, the structure being sufficiently weak that a traction applied to the flexible extension displaces the sleeve into the end position.

2. The protective device defined in claim 1 wherein the structure is a thin frangible web connecting the sleeve inner end to the end fitting.

3. The protective device defined in claim 2, further comprising
   a generally inextensible tether having one end connected to the end fitting and another end connected to the sleeve, the tether being dimensioned such that it is taut in the end position of the sleeve.

4. The protective device defined in claim 3, further comprising
   a stiff end cap fittable over the needle and formed with a slot through which the tether passes when the tether is fitted over the needle.

5. The protective device defined in claim 2, wherein the end fitting is formed with at least two outwardly projecting tongues engaged in the sleeve in the starting position.

6. The protective device defined in claim 1 wherein the structure is flexible and extensible, the structure being longitudinally compacted in the starting position and longitudinally extended in the end position.

7. The protective device defined in claim 6 wherein the structure can telescope.

8. The protective device defined in claim 6 wherein the structure is formed at least partially as a bellows.

9. The protective device defined in claim 6, further comprising
   a stiff end cap fittable over the needle and having an inner end attached to the outer end of the sleeve.

10. The protective device defined in claim 1 wherein the end fitting is rotation symmetrical.

11. The protective device defined in claim 1 wherein the sleeve has an inner wall provided with spring tongues directed to resist movement of the sleeve from the end position into the starting position.

12. The protective device defined in claim 1 wherein the sleeve outer end is formed with inwardly open pockets dimensioned to catch the needle tip on displacement of the sleeve from the end position to the starting position.

13. The protective device defined in claim 1 wherein the sleeve is provided with latch means for retaining it in the end position.

14. The protective device defined in claim 1 wherein the inner sleeve end is inwardly flared.

15. The protective device defined in claim 1 wherein the extension is generally parallel to the needle and has an inner end attached to the sleeve inner end.

* * * * *